United States Patent
Madsen et al.

(10) Patent No.: US 6,893,415 B2
(45) Date of Patent: May 17, 2005

(54) MEDICATION DELIVERY DEVICE

(75) Inventors: Mads Koerstz Madsen, Herlev (DK); Jens Munk, Stenløse (DK)

(73) Assignee: Novo Nordisk A/S, Bagsvaerd (DK)

( * ) Notice: Subject to any disclaimer, the term of this patent is extended or adjusted under 35 U.S.C. 154(b) by 429 days.

(21) Appl. No.: 09/960,245

(22) Filed: Sep. 21, 2001

(65) Prior Publication Data

US 2002/0133113 A1 Sep. 19, 2002

Related U.S. Application Data

(60) Provisional application No. 60/237,902, filed on Oct. 4, 2000.

(30) Foreign Application Priority Data

Sep. 22, 2000 (DK) .......................... 2000 01406

(51) Int. Cl.$^7$ ............................................. A61M 31/00
(52) U.S. Cl. ......................................... 604/65; 604/151
(58) Field of Search ................................ 604/151–152, 604/154, 187, 207, 208, 65–67, 235; 128/DIG. 1

(56) References Cited

U.S. PATENT DOCUMENTS

| | | |
|---|---|---|
| 3,944,843 A | 3/1976 | Vaz Martins |
| 4,950,246 A | 8/1990 | Muller |
| 5,820,602 A | 10/1998 | Kovelman et al. |
| 5,879,360 A | 3/1999 | Crankshaw |
| 5,879,630 A | 3/1999 | Lescouzeres et al. |
| 5,928,201 A * | 7/1999 | Poulsen et al. ............. 604/208 |
| 5,933,671 A | 8/1999 | Stephany et al. |
| 5,989,221 A | 11/1999 | Hjertman |

FOREIGN PATENT DOCUMENTS

| | | |
|---|---|---|
| EP | 017 318 | 10/1980 |
| EP | 454 331 | 10/1991 |
| EP | 615 762 | 9/1994 |
| EP | 1 074 273 | 2/2001 |
| GB | 2153445 | 8/1985 |
| GB | 2229497 | 9/1990 |
| WO | WO 85/02256 | 5/1985 |
| WO | WO 97/33638 | 9/1997 |
| WO | WO 99/07425 | 2/1999 |

* cited by examiner

*Primary Examiner*—Loan H. Thanh
(74) *Attorney, Agent, or Firm*—Reza Green, Esq.; Richard W. Book, Esq.; Marc A. Began, Esq.

(57) ABSTRACT

A medication delivery device comprising a system that is able to sense if the delivery device is in actual physical contact with a human being or if the delivery device has been abandoned. The system comprises an electronic control and a touch sensitive switch preferably formed as a part of the housing of the medication delivery device. The housing can be divided into two parts each constituting separate electrical conductors being spaced apart from each other by an insulating material. When the two parts a temporarily bridged e.g. by the skin of a human being a direct current path between the parts are created, which can provide an electrical signal at the electronic control. When a dose has been set, absence of the signal will cause the electronic control to cancel the set dose and to sound an alarm.

4 Claims, 2 Drawing Sheets

MEDICATION DELIVERY DEVICE

This application claims priority on U.S. provisional patent application No. 60/237,902 filed on Oct. 4, 2000.

The invention relates to a medication delivery device of the kind delivering medicine or other fluent material from a cartridge and into a human body, and more specifically to a safety appliance for such a medication delivery device.

Medical injection devices are used to deliver liquid medication to patients. Some medicine, such as insulin is self-administered. The typical diabetes patient will require injections of insulin several times during the course of the day. The required dose of insulin will vary from patient to patient, and may for each patient vary during the course of the day and from day to day. Each diabetes patient will establish a regimen that is appropriate for his or her own medical condition and for his or her lifestyle.

Mechanical medication delivery devices facilitating the self-administration of insulin have been known for several years. Such a mechanical medication delivery device comprises a cartridge containing medicine sufficient for a number of therapeutic doses, and a piston movable mounted in the cartridge. The piston is moved forward inside the cartridge by a piston rod, which is driven by a mechanical drive mechanism. The patient moves the piston forward and injects the medicine by physically pressing back a push button into its initial position. The push button is lifted away from its initial position when the patient dials up the size of the dose to be injected, utilizing a dose setting mechanism. Recently an electronic monitored, but mechanical operated medication delivery device having an electronic display, displaying the mechanical set dose has been developed. This device is presented in WO 97.33638.

Another type of a medication delivery device having a motorized dose setting is shown in U.S. Pat. No. 5,928,201. In this medication delivery device an electrical motor is used for setting up the dose by moving some mechanical dose setting elements relative to each other. One of the dose setting elements is the delivery button, which is moved away from its original position by the electrical motor. The motor can be controlled to run as well clockwise as anticlockwise in order to increase or decrease the size of the dose, which dose is shown on an electronic display. In order to inject the set dose, the delivery button is manually pressed back to its original position by the user.

Within the last few year is has become more common to manufacture medication delivery devices where the whole of the mechanical drive mechanism is substituted with an electrical motor, such that the motor carries out the injection. A prior art medical delivery device of this type is shown in U.S. Pat. No. 4,950,246. This medical delivery device comprises a cartridge containing the medicine, and a piston movable mounted inside the cartridge. The piston is moved forward inside the cartridge by a piston rod, which is driven by an electrical motor controlled by an electronic control unit. Pushing or pressing a button located on the medical delivery device starts the delivery of the set dose, which dose is set up by pressing a dose setting button provided on the exterior of the housing. When setting up a dose, the size of the set dose is read into the electronic control unit, and shown on a display also provided on the housing of the medication delivery device.

For a diabetic patient using a medication delivery device for insulin, there is a potential safety risk that a child, or any other non-diabetic person, by accident, gets a medication delivery device, that has already a preset dose of insulin ready to be injected, in there hands. This can happen when the diabetic patient, after setting up a dose, is distracted e.g. by a telephone ringing, and leaves the medication delivery device unattended on a table or the like. The child could then by accident get the preset dose injected into him or her self, which would present a serious risk for the child or the non-diabetic person.

Another safety problem is the potential risk that a preset dose by accident is altered, which could happen if the medication delivery device is dropped onto the ground. This might result in the diabetic patient getting a larger or a smaller dose of insulin than expected, which will cause a serious risk to the health of the diabetic patient.

It is an object of the present invention to provide a medication delivery device, which does not posses the drawbacks of the prior art medication delivery devices, and where it is possible to leave the medication delivery device unattended without exposing people in the surroundings to a safety problem.

Another object of the present invention is to provide a medication delivery device, which will react when left unattended.

It is further an object of the present invention to provide a medication delivery device, which has a safety system able to sense when in contact with a human being and when not.

This is obtained by a medication delivery device comprising;

a housing accommodating a cartridge from which medicine can be pressed out through a needle or the like mounted at the distal end of said cartridge when an injection button is operated, which medicine is pressed out by driving a piston forward inside said cartridge, and an electronic control unit into which the size of a set dose can be read by operation of a dose setting button located on said housing, said set dose being displayed in a display provided in said housing, and which electronic control unit is communicating with drive means located inside said housing, said drive means driving forward a piston rod abutting said piston inside said cartridge in accordance with said set dose when said injection button is operated, which medication delivery device according to the invention is characterized in that A sensor is located on said housing, which sensor provides a signal to said electronic control unit when said sensor is activated by physical contact with a human being.

As long as the medication delivery device is in the hands of the user the sensor located on the housing senses this, and transmits a signal to the electronic control unit, while when the user abandons the medication delivery device the signal ceases to be transmitted to the electronic control unit. Both the absence and the presence of such a signal can be used to implement greater safety, both for the user and for people in the surroundings. When the electronic control unit detects the absence of a signal from the sensor, the electronic control unit can either immobilize or reset the medication delivery device, or both. The absence of the signal can also be used to switch off the medication delivery device. Whenever the user grasps the medication delivery device, the sensor detects this and starts delivering the signal to the electronic control unit. The presence of the signal can be used to turn on the medication delivery device or to display or sound stored information.

When, the sensor is a touch sensitive switch sensitive to the touch of a human being, it is ensured that the signal will be provided whenever the medication delivery device is simply located in the hand of the user, without the user having to push or to press a button.

When, the sensor is a part of the housing, it is ensured that the surface of the housing can be design very smooth without any protruding buttons.

When, the sensor comprises two parts or contacts each constituting separate electrical conductors being spaced apart from another by an insulating material, and that the two parts when temporarily bridged e.g. by the skin of human being, allows a direct current path between the two parts, it is ensured that the signal is provided simply by having the medication delivery device touch the skin of a human being, or in fact the skin of any mammal body.

In one embodiment of the medication delivery device according to the invention, the two parts and the insulating material together define the housing. Two parts, which do not necessarily have to be the same size, being separated from each other only by the insulating material can make up the entire housing, such that the outer surface of the housing only constitutes of a total of three parts. In this way it is ensured that that the two half-parts are always bridged when the device is in the hand of a user.

When, the absence of the signal over a period of time causes the electronic control means to immobilize the injection button, in this way it is ensured that a set dose cannot be injected when the medication delivery device is no longer in contact with a human being.

When, the absence of said signal over a period of time causes said electronic control means to output an error message, it is ensured that the user is informed of the current status of the medication delivery device. The error message could e.g. be an audible alarm signal, or it could be a readable message appearing in the display When, the housing is provided with means for setting up the dose to be injected, and that the absence of the signal over a period of time causes the electronic control means to cancel the set up dose to be injected, it is ensured that the user has to set up a new dose whenever the device has been abandon. If the user e.g. drops the device on to the ground and the set dose is altered, this altered dose will automatically be cancelled when the medication delivery device is out of touch with the user In yet another embodiment the drive means comprises an electrical motor, which is activated by the injection button. When the injection button is activated it energized the electrical motor, which then moves the piston rod and the piston forward inside the cartridge in order to expel an amount of medicine according to the set dose. The injection button could be an ordinary push button, or it could be a touch sensitive button.

If the medication delivery device is a fully mechanical medication delivery device having a display displaying the mechanical set dose, the presence or absence of the signal from the sensor can be used to display a predetermined message in the electronic display, or to sound an alarm. Since a mechanical medication device is not equipped with an electrical motor it is not possible automatically to cancel an already set dose, however the medication delivery device could be equipped with means for immobilizing the device when the signal from the sensor is missing.

The invention will be explained more fully below in connection with a preferred embodiment and with reference to the drawings in which:

FIG. 4 illustrates two contacts disposed on a housing in accordance with a non-limiting embodiment of the present invention.

The figures are schematic and simplified for clarity, and they just show details, which are essential to the understanding of the invention, while other details are left out. Throughout, the same reference numerals are used for identical or corresponding parts.

Figure 1:
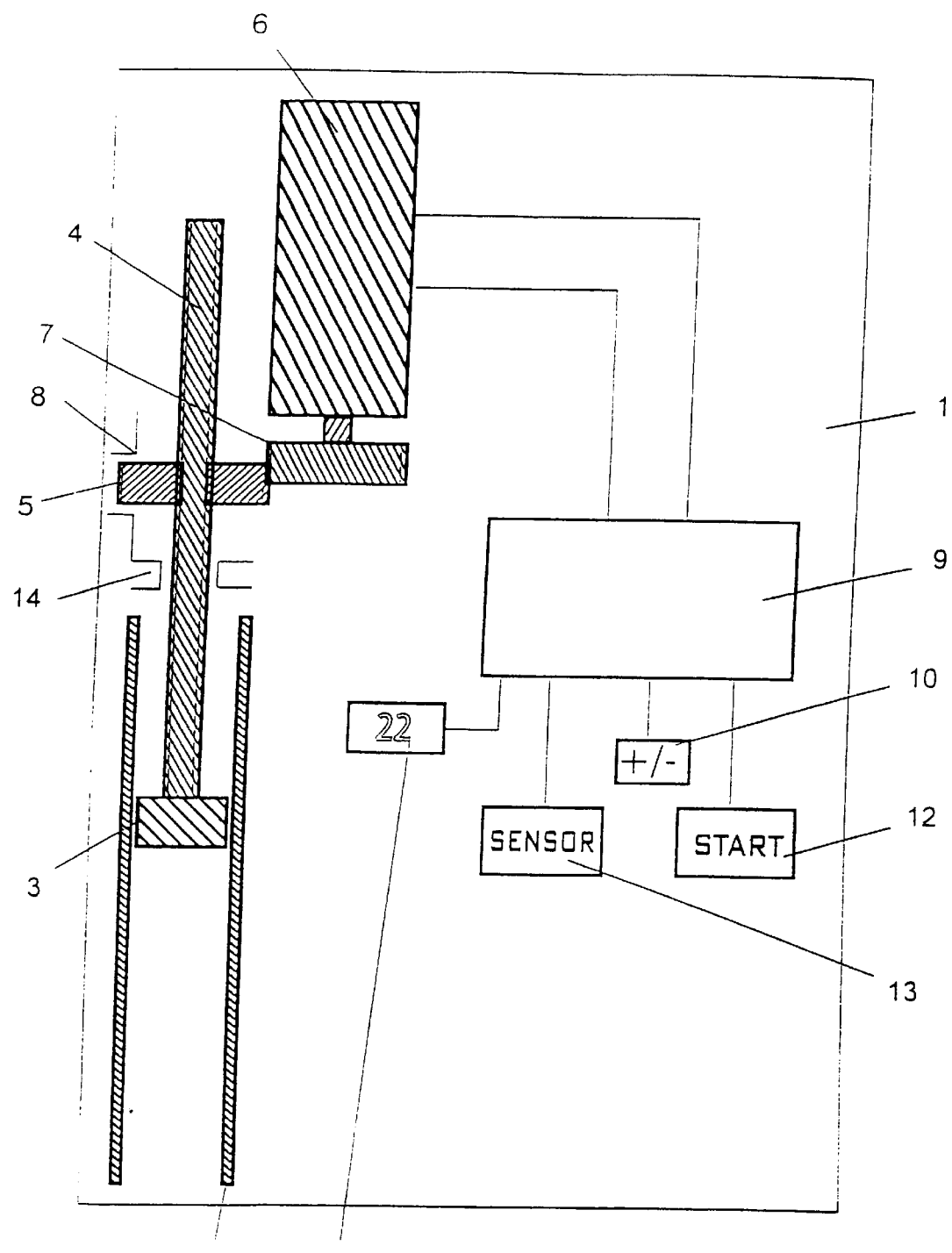
FIG. 1 Shows a schematic drawing of the electronic medication device according to the invention.
Figure 2:
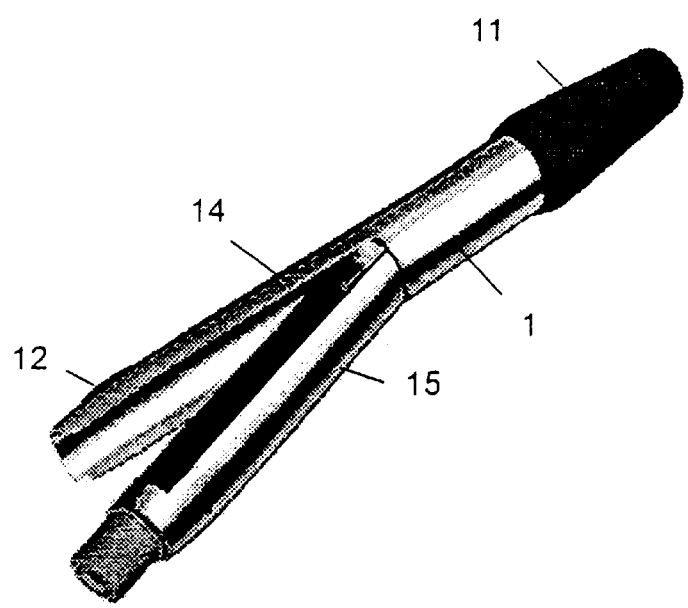
FIG. 2 Shows a medication delivery device according to an embodiment of the invention.

The electronic medication delivery device shown in FIG. 1 comprises a housing 1 containing a cartridge 2 inside which a piston 3 is located. The piston 3 is moved forward inside the cartridge 2 by a piston rod 4. The piston rod 4 has an external helical thread, which fits the internal thread of a nut 5. The nut 5 is rotated by an electrical motor 6 through a gearing wheel 7. The nut 5 is longitudinal locked relatively to the housing 1 e.g. by a pair of shoulders 8 provided in the housing 1

The piston rod 4 is locked against rotation e.g. by a number of protrusions 14 provided in the housing 1, which protrusions 14 engages a longitudinal recess in the piston rod 4. Thereby rotation of the nut 5 is transmitted to a longitudinal movement of the non-rotational piston rod 4.

Figure 3:
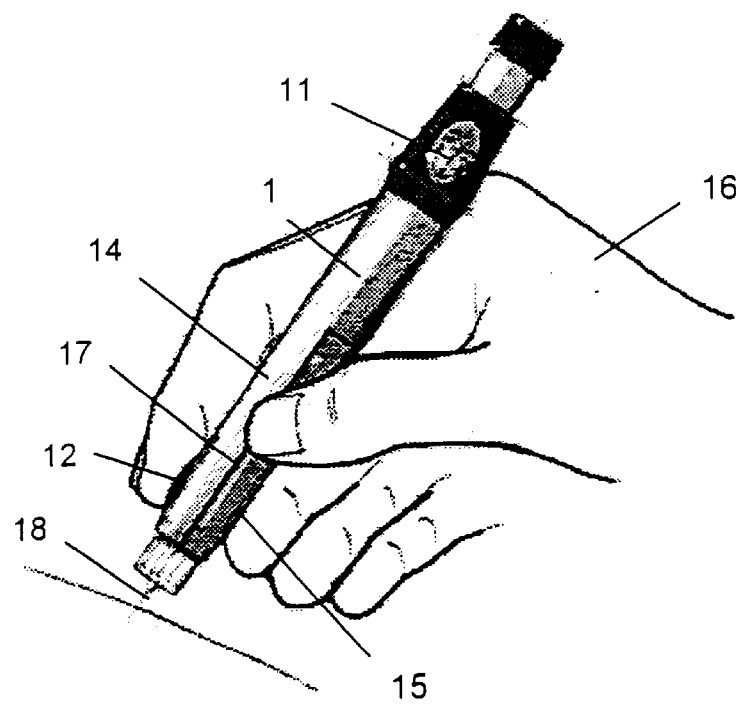
FIG. 3 Shows the medication delivery device shown in FIG. 2 in the hand of a user.

The distal end of the cartridge 2 is usually closed by a closure enabling the mounting of an injection needle 18, as shown in FIG. 3. Another form of conduit such as a catheter could however be mounted if so wanted. When the electrical motor 6 is activated, the motor rotates the gearing wheel 7 causing the nut 5 to rotate. Since the nut element is longitudinal locked to the housing 1, the rotation of the nut 5 forces the piston rod 4 to move the piston 3 forward inside the cartridge 2, which results in the liquid medicine contained in the cartridge 2 being pressed out through the needle 18.

The motor 6 is activated by an electronic control unit 9, which could be a programmable microprocessor receiving inputs from various switches and buttons located on the medical delivery device, and returning outputs according to a stored program.

The dose to be injected is set by activating the dose setting button 10 for counting forward or backward. Instead of one dose setting button 10, two buttons can be provided, one for counting up and one for counting down. The set dose is stored in the electronic control unit 9 and is displayed on the display 11. As long as the dose setting button 10 is pressed the set dose is increased or decreased and the size of the dose may currently be followed on the display 11.

The motor 6 which may be controlled to run as well clockwise as anticlockwise is controlled from the electronic control unit 9 to rotate the nut 5 in accordance with the set dose. The injection is started by pressing the start button 12, which activates the electrical motor 6 to rotate the nut 5 according to the set dose.

The housing is also provided with a sensor 13, which senses if the medication delivery device is in the hand 16 of the user. The sensor, which can be touch sensitive, is preferably made up from two parts 14, 15, which two parts 14, 15 is made from a conductive material and spaced from one another by a non-conductive insulating material 17. The sensor 13 is located in an area on the exterior of the housing 1 of the medication delivery device, which is certain to be touched by the hand 16 of the user when handling the medication delivery device. When the skin on the finger of the user bridges the two conductive parts 14, 15, as shown in FIG. 3, a direct current path is temporally created between the two parts 14, 15. A signal can then be transmitted to the electronic control unit 9.

Touch sensitive electronic sensors of the type used in the present invention is e.g. known from U.S. Pat. No. 5,933, 671 and U.S. Pat. No. 3,944,843, in which patents a detailed description is available.

When the user abandons the medication delivery device the two parts 14, 15 is no longer in electrical communication with each other, and as a result no signal are transmitted to the electrical control unit 9. When the electronic control unit 9 detects that no signal is being received from the sensor 13, the electronic control unit 9 immobilizes the start button 12, such that the electrical motor 6 cannot be activated. At the same time the electronic control unit 9 resets the set dose.

The operation of the medication delivery device is as follows. The user holds the medication delivery device in his or her hand 16 and set the size of the dose to be injected by pressing the dose setting button 10. Once the size of the dose has been set, the needle 18 is injected into the skin of the user and the start button 12 is pressed. If the user is disturbed after the size of the dose has been set, and leaves the medication delivery device unattended on a table or the like, the electronic control unit 9 detects the absence of the signal from the sensor 13 and immobilizes the start button 12 and resets the set dose. This will prevent a non-diabetic person picking up the medication delivery device from injecting him or her self.

The immobilization of the start button 12 can be restricted only to be valid for a period of time, or until a new dose has been set. The electronic control unit 9 can also be programmed only to immobilize the start button 12, or to reset the set dose, when the signal from the sensor has been absent for a certain period of time.

Instead of providing the sensor 13 in an area of the housing, the sensor 13 it self can constitute a part of the housing 1 or the entire housing. This can e.g. be done by making the entire housing only from the two parts 14, 15 being separated by the insulating material 17. However the sensor 13 can be made in many different ways; capacitive, changes in an oscillator, heat, infrared or light reflection without departing from the scope of the present invention.

When the signal from the sensor 13 has been absent for a predetermined period of time and the set dose is reset, the electronic control unit 9 can be programmed to output an error message, which could be an acoustic signal and/or a written message readable in the display 11.

Some preferred embodiments have been shown in the foregoing, but it should be stressed that the invention is not limited to these, but may be embodied in other ways within the subject matter defined in the following claims. Instead of only utilizing the absence of the signal from the sensor, it could for example be possible to use the presence of the signal to turn on the medication delivery device or to recall information stored in a memory function.

All though the explanation given primarily concerns a medication delivery device utilizing a motor for carrying out the injection, it is obvious that a motor is not a necessity for carrying out the invention according to the claims. A sensor transmitting a signal to an electronic control unit when the sensor is activated by physical contact with a human being can easily be provided on the housing of a fully mechanical medication device having an electronic display displaying the mechanical set dose without departing from the scope of the claims. The presence or absence of the signal from the sensor can then be used to display a predetermined message in the electronic display, or to sound an alarm. The absence of the signal could even be used to activate a mechanism, which locks the injection button such that the next person holding the medication delivery device is prevented from manually pressing home the injection button until the lock has been deactivated.

What is claimed is:

1. A medication delivery device comprising:
    a. housing for accommodating a cartridge of a medicament, which has a moveable piston sealing one end of the cartridge and which is capable of being coupled to an injection needle so that medicament in the cartridge can be pressed out through the needle when the piston is moved in a first direction;
    b. a piston rod for driving the piston in the cartridge to expel medication from the cartridge;
    c. a electric drive coupled to the piston rod;
    d. an electronic control unit communicating into which the size of a desired dose can be inputted by a user; wherein the electronic control unit communicates with the electric drive to drive the piston rod;
    e. a touch sensor sensitive to the touch of a human being, the sensor comprising two parts, each constituting separate electrical conductors spaced apart from one another, such that when the two parts are temporarily bridged by the skin of a human being a direct current path between the two parts is established, and
    f. wherein the touch sensor is in communication with the control unit so that the control unit receives a signal when the sensor is in contact with human skin.

2. The medication delivery device of claim 1, wherein the touch sensor is incorporated into the housing.

3. A medication delivery device comprising:
    a housing accommodating a cartridge from which medicine can be pressed out through a needle mounted at the distal end of said cartridge when an injection button is operated, wherein the medicine is pressed out by driving a piston forward inside said cartridge, and an electronic control unit into which the size of a set dose can be read by operation of a dose setting button located on said housing, said set dose being displayed in a display provided in said housing, and wherein an electronic control unit is in communication with piston rod drive mechanism that drives forward a piston rod that abuts the piston inside said cartridge, wherein the piston is drive a distance corresponding to the set dose when said injection button is operated, wherein a touch sensitive switch sensitive to the touch of a human being is provided, said switch comprising two parts each constituting separate electrical conductors spaced apart from another by an insulating material, such that said two parts when temporarily bridged, by the skin of human being, allows a direct current path between said two parts.

4. The injection device according to claim 3, wherein the two parts are integrated with the housing so that the touch sensor is an integral part of the housing.

* * * * *